(12) United States Patent
Benenati et al.

(10) Patent No.: US 11,510,802 B1
(45) Date of Patent: Nov. 29, 2022

(54) SCOLIOSIS BRACE

(71) Applicant: East Coast Orthotic & Prosthetic Corp., Deer Park, NY (US)

(72) Inventors: Vincent A. Benenati, Deer Park, NY (US); Diogo Roquette Osorio, Deer Park, NY (US)

(73) Assignee: Vincent Benenati, Dix Hills, NY (US)

( * ) Notice: Subject to any disclaimer, the term of this patent is extended or adjusted under 35 U.S.C. 154(b) by 0 days.

(21) Appl. No.: 16/926,705

(22) Filed: Jul. 12, 2020

Related U.S. Application Data

(60) Provisional application No. 62/873,845, filed on Jul. 12, 2019, provisional application No. 62/873,846, filed on Jul. 13, 2019.

(51) Int. Cl.
*A61F 5/02* (2006.01)

(52) U.S. Cl.
CPC ............... *A61F 5/028* (2013.01); *A61F 5/02* (2013.01); *A61F 5/022* (2013.01); *A61F 5/024* (2013.01); *A61F 5/026* (2013.01)

(58) Field of Classification Search
CPC .. A61F 5/01; A61F 5/0102; A61F 5/02; A61F 5/022; A61F 5/024; A61F 5/026; A61F 5/028; A61F 5/37; A61F 5/3715; A61F 5/3723; A61F 5/3753; A61F 5/03; A61F 5/042; A61F 2005/0197; A61F 2005/0167; A61F 2005/0158; A61L 15/00; A61L 15/07; A61H 1/008; A41D 13/0531; A41D 13/0568; A41D 13/05; G06Q 50/22; G06Q 50/10; G16H 10/60; G01B 11/24; A45F 2003/007; A45F 2003/025; A45F 2003/045; A45F 2003/127; A45F 3/00; A45F 3/04; A41F 9/00; A41F 9/002; A41F 11/00
USPC .......................................................... 602/19
See application file for complete search history.

(56) References Cited

U.S. PATENT DOCUMENTS

| | | | |
|---|---|---|---|
| 2013/0303956 A1* | 11/2013 | Anglada | A61F 5/028 602/19 |
| 2014/0296759 A1* | 10/2014 | Matthews | A61F 5/024 602/19 |
| 2014/0330187 A1* | 11/2014 | Perez | A61F 5/028 602/19 |

(Continued)

FOREIGN PATENT DOCUMENTS

WO WO-2018186553 A1 * 10/2018 ............. G01B 11/24

*Primary Examiner* — Alireza Nia
*Assistant Examiner* — Daniel A Miller
(74) *Attorney, Agent, or Firm* — Curran Patent Law; Kevin Curran, Esq.

(57) ABSTRACT

This invention relates to a three-dimensional scoliosis support system capable of providing pain relief and improvement of the spinal balance in scoliosis patients with different curve types. The disclosed bracing system is a tension-based scoliosis orthosis that comprises an rigid back panel. The three de-rotational supports pads of the back panel are connected to each other, providing facilitation or restriction of certain movements of human spine in the three different anatomical planes, i.e., coronal, sagittal and transverse planes. This scoliosis brace includes inelastic straps connected to the de-rotational supports/pads of the back panel, and the bracing system has different sizes and it can be fitted and adjusted accordingly with scoliosis curve type and patient characteristics.

20 Claims, 19 Drawing Sheets a plan view image of a front side of an exemplary embodiment of the invention.

(56) References Cited

U.S. PATENT DOCUMENTS

2019/0117432 A1* 4/2019 Park .................. A61F 5/026

* cited by examiner

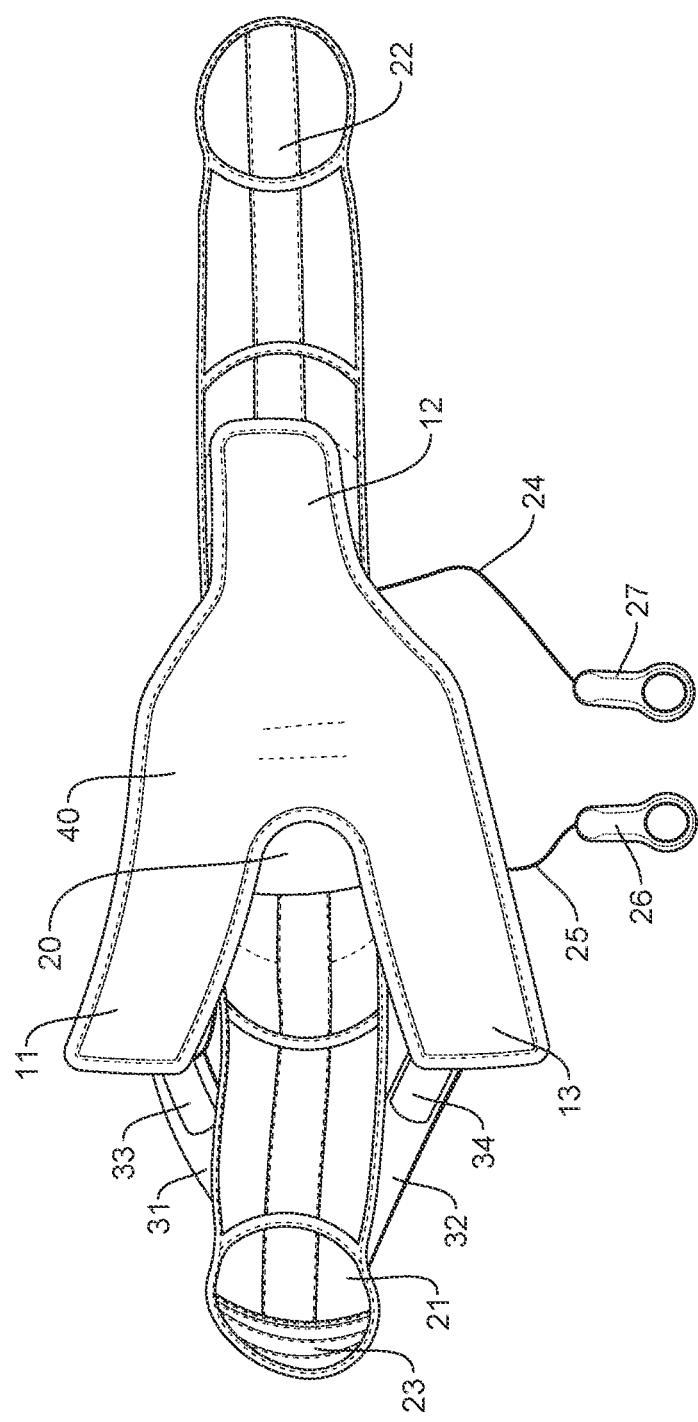
Figure 1 - shows a plan view image of a front side of an exemplary embodiment of the invention.

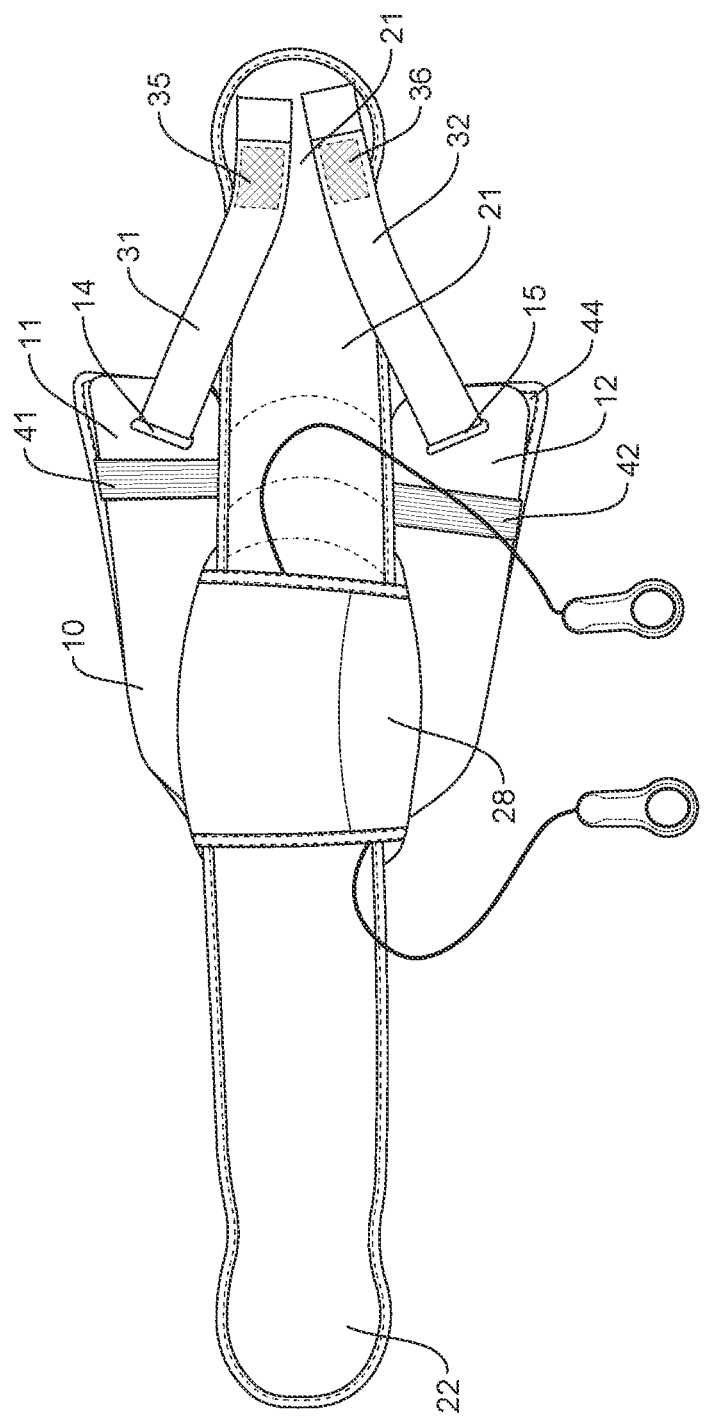
Figure 2- shows a plan view image of a back side of the exemplary embodiment of FIG. 1.

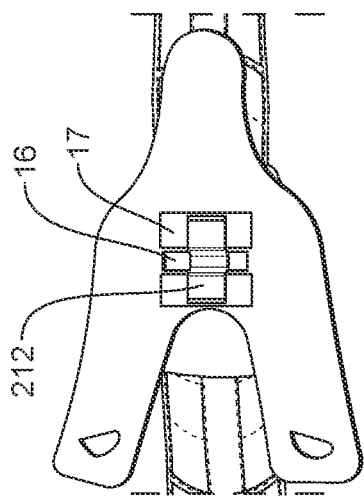
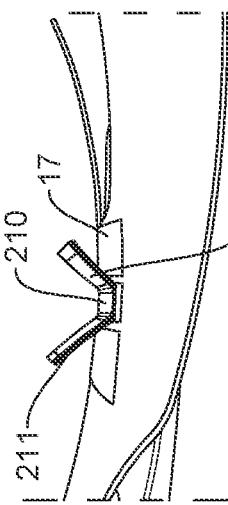
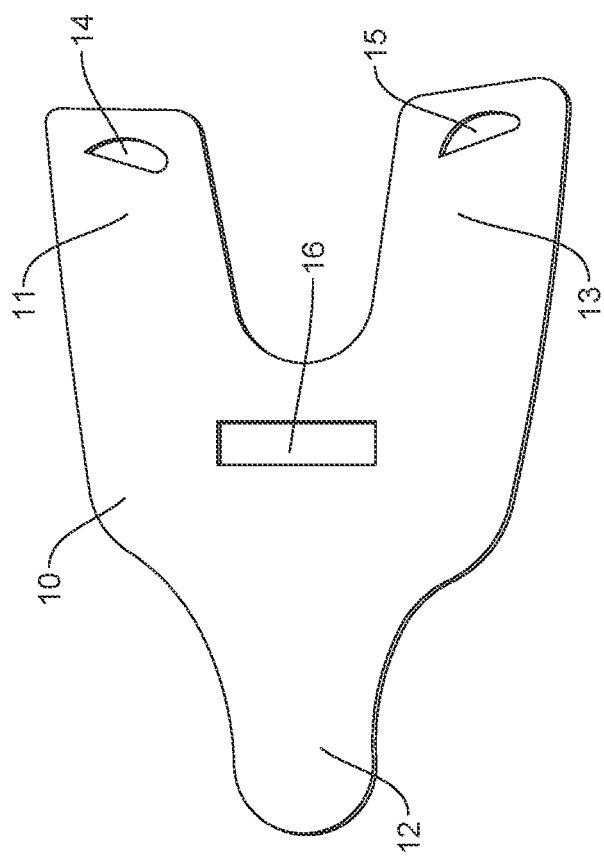
Figures 3A-3C - show a plan view and perspective view images of the innovative rigid back panel and adjustable Velcro hook and loop system/fastener on the inner face of the back piece that will attach with the lumbar belt.

Figures 4A-4D - show images of the straps of the de-rotational pads of the rigid back panel of FIG. 2.

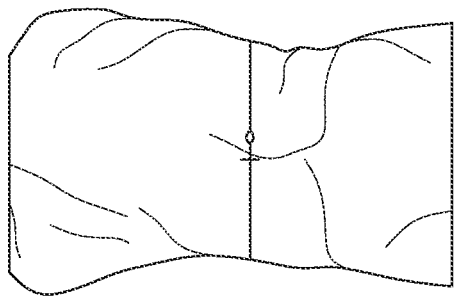

Fig. 5C

Typical posterior view of a body of a person with a Left Lumbar/Thoracolumbar Scoliosis.

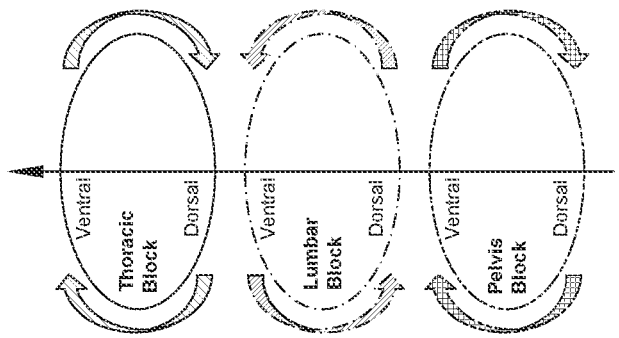

Fig. 5B

This figure illustrates the direction of the rotation of the different blocks of the spine of a person with a Left Lumbar/Thoracolumbar Scoliosis. When viewing from the top the lumbar block is rotated in the anti-clockwise direction and the other structural blocks of the spine (thoracic and pelvic) are rotated in the clockwise direction.

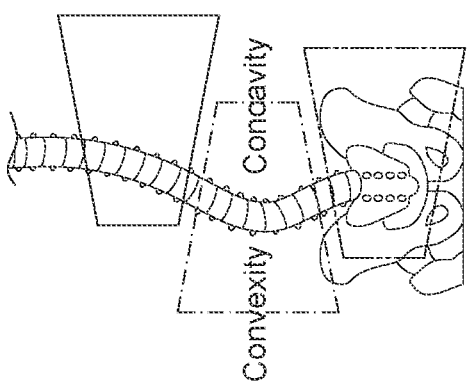

Fig. 5A

Typical posterior view of an x-ray of a person with a Left Lumbar/Thoracolumbar Scoliosis. This illustration shows also a relationship of the deformity with the different structural blocks of the spine (Pelvis, Lumbar/Thoracolumbar and Thoracic).

Figures 5A-5C – show illustrations of an x-ray and rotation mechanism in the different structural blocks of the spine (thoracic, lumbar/thoracolumbar and pelvis) and body of a person with a left Lumbar/Thoracolumbar Scoliosis.

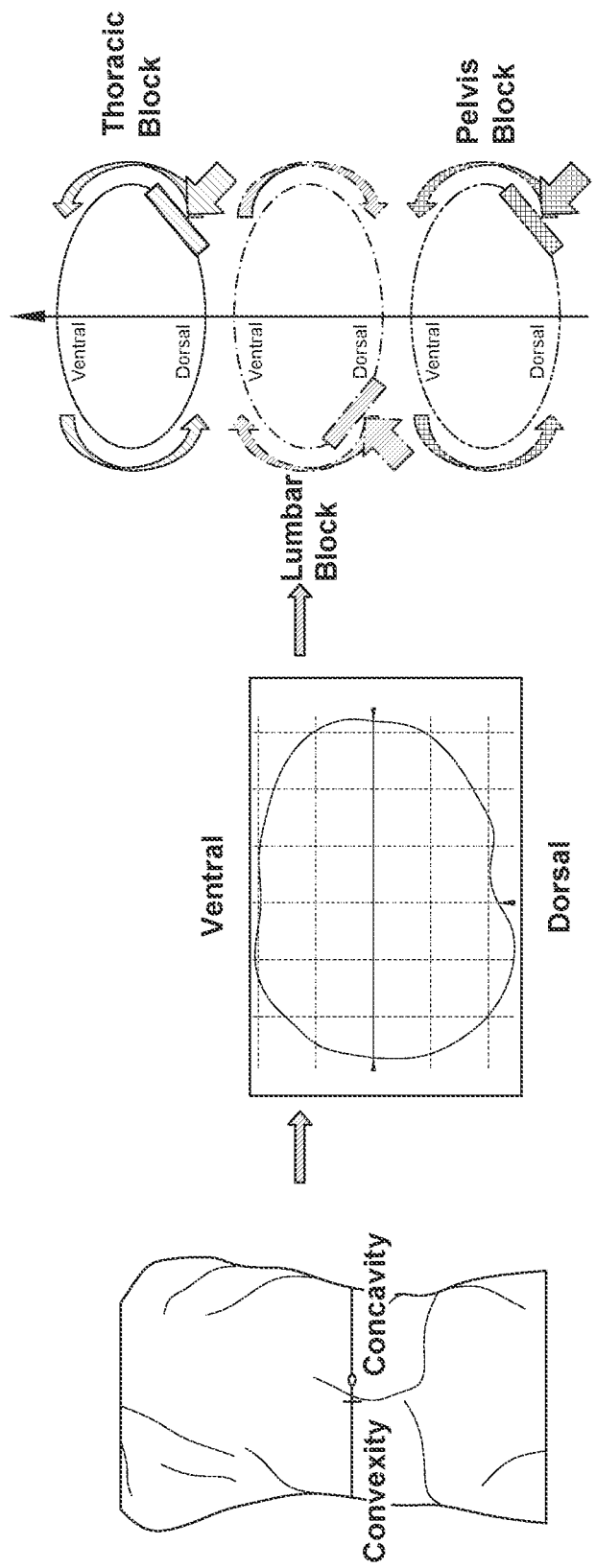
Figures 6A-6C – show illustrations of appropriate application of the de-rotational forces of the tension-based scoliosis orthosis.

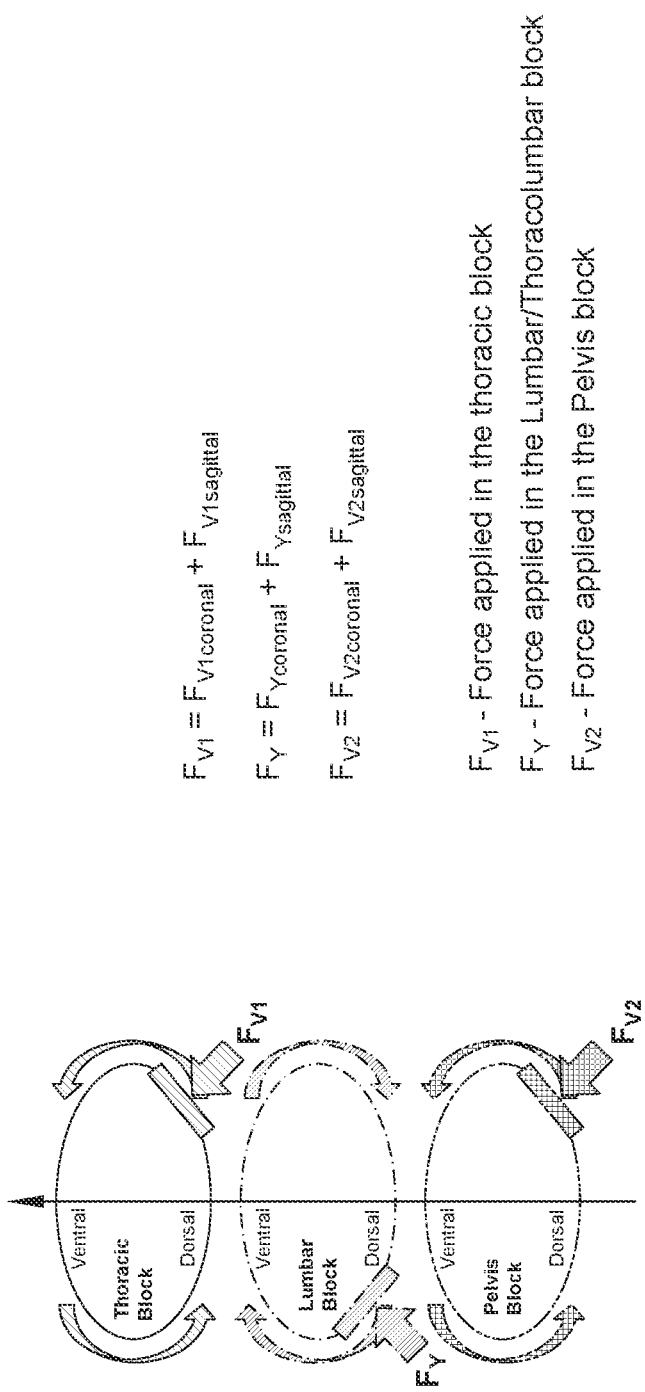
Figures 7A-7B - show the de-rotational forces applied in a wearer body with Left Lumbar/Thoracolumbar Scoliosis. Each de-rotational force has two components, the component of the coronal plane and the component of the sagittal plane.

Figures 8A-8B - show the components of the de-rotational forces that are going to form in the coronal plane the three-point force system.

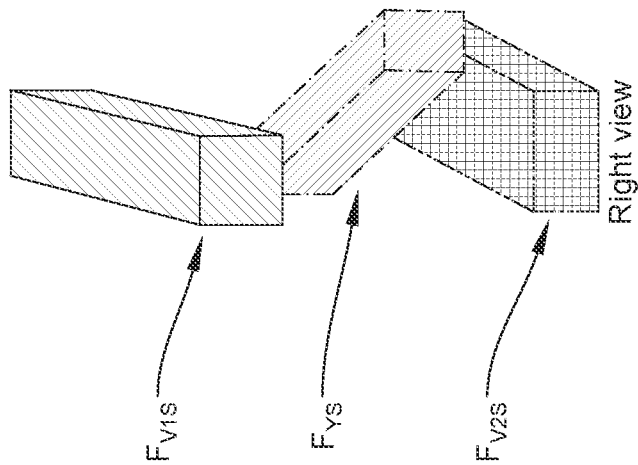
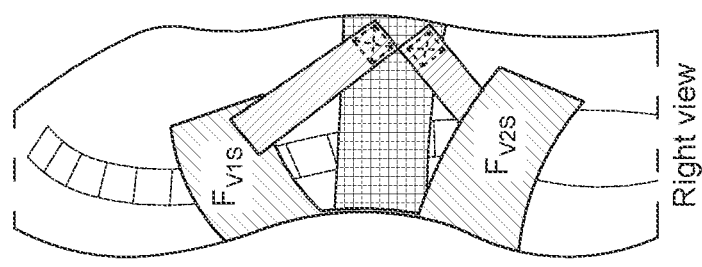
Figures 9A-9B - shows illustrations of the components of the de-rotational forces in the sagittal plane.

Figures 10A-10C - show illustrations to describe the adjustment of the direction and magnitude of the de-rotational forces by using additional pads.

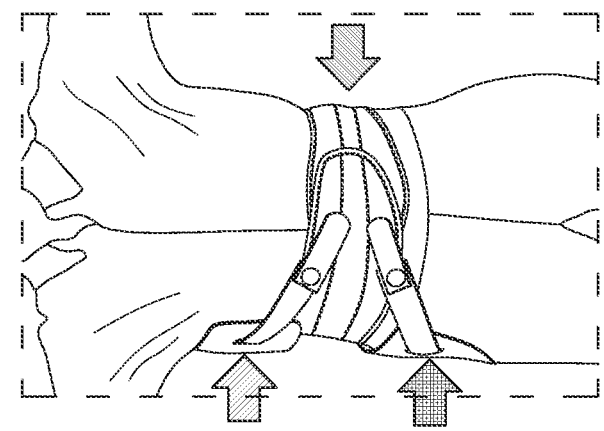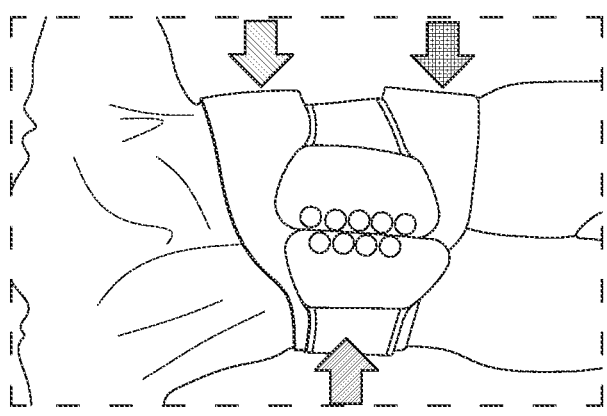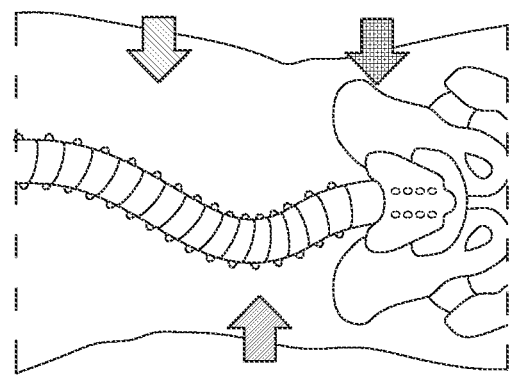

FIG. 11A — Typical Posterior View of a body of a person with a Left Lumbar/Thoracolumbar Curve FIG. 11B — Posterior View of a wearer using the scoliosis tension-based system adapted to a person with a left Lumbar/Thoracolumbar scoliosis FIG. 11C — Anterior view of a wearer using the scoliosis tension-based system adapted to a person with a left Lumbar/Thoracolumbar scoliosis Figures 11A-11C - show images of setup of the disclosed tension-based scoliosis system for a person with a Left Lumbar/Thoracolumbar scoliosis curve.

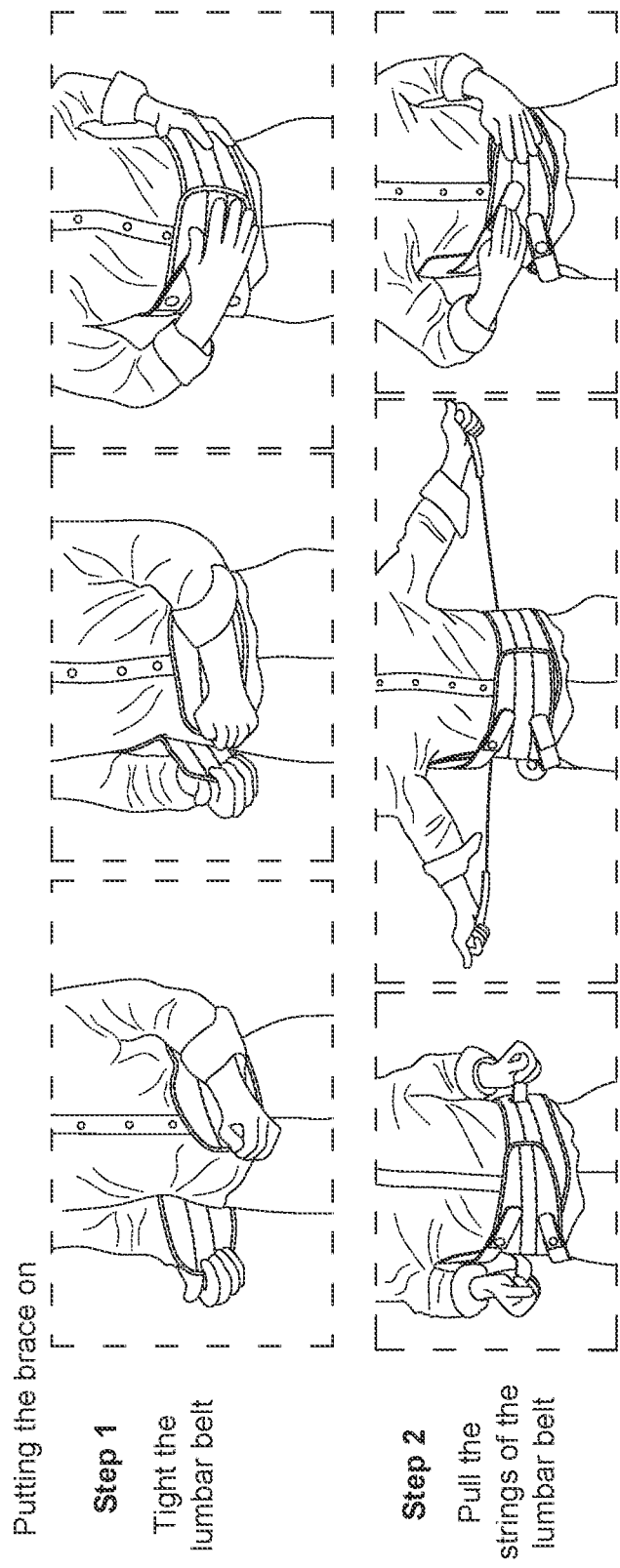
Figure 12 - shows images of the sequence of a wearer putting the brace on. Bracing system for a Left Lumbar/Thoracolumbar scoliosis curve.

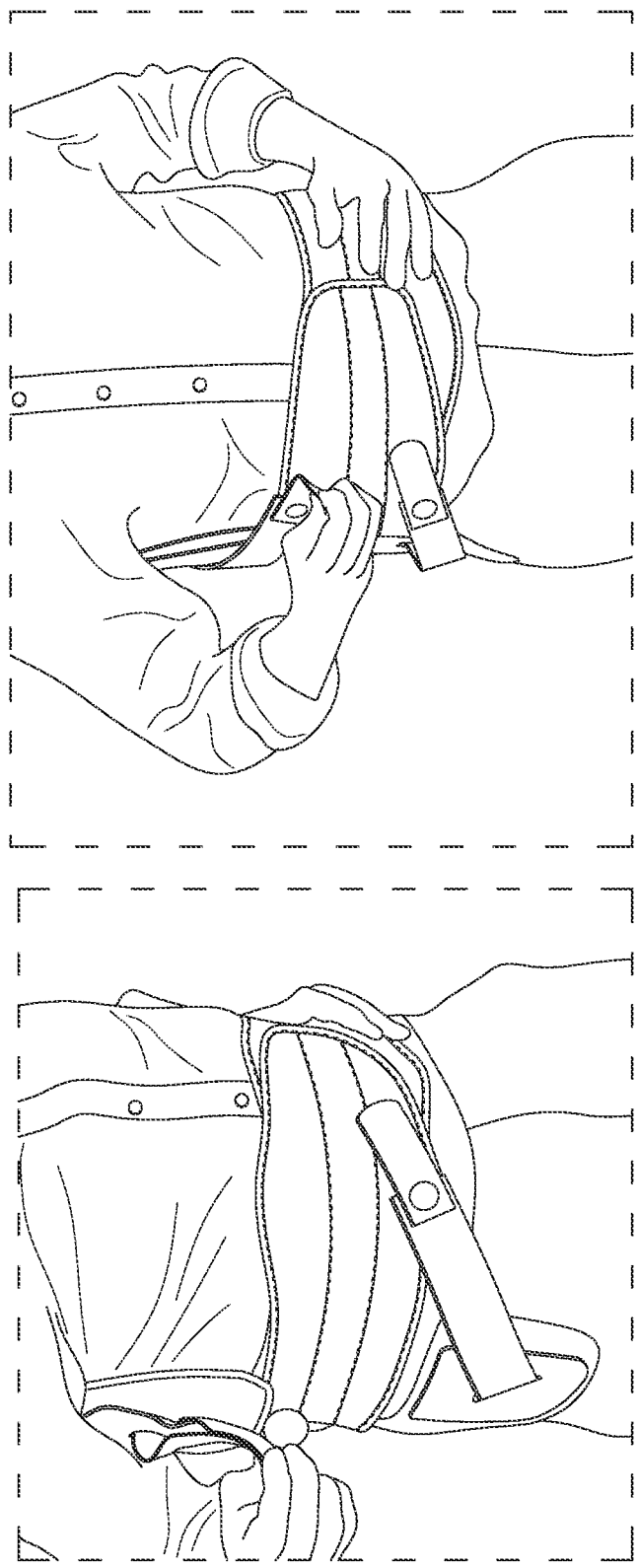
Figure 13 - shows images of the adjustment of the strap tension of the de-rotational forces of the thoracic pad.

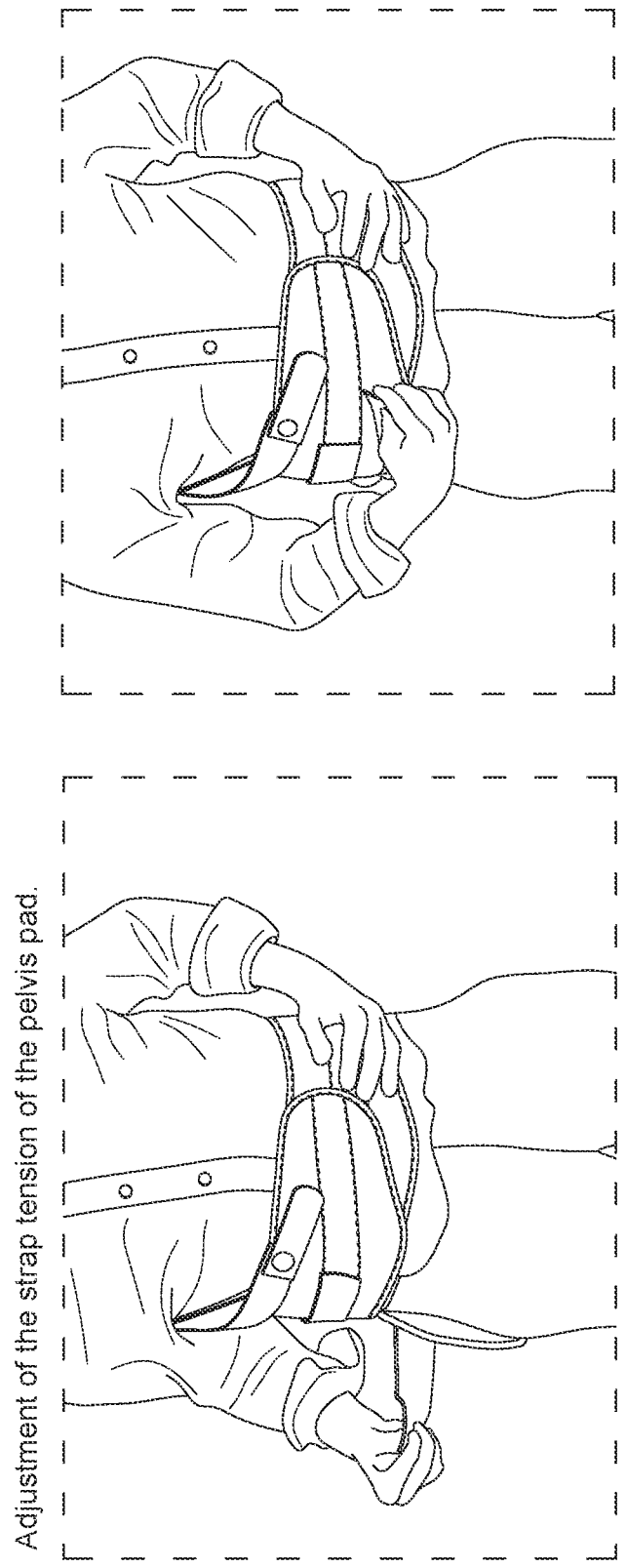
Figure 14 - shows images of the adjustment of the strap of the de-rotational forces of the pelvis pad.

Figures 15A-15D - depict the Setup of the tension-based scoliosis system for a person with a Right Lumbar/Thoracolumbar scoliosis curve.

Figures 16A-16D - depict the Setup of the tension-based scoliosis system for a person with a Right Thoracic scoliosis curve.

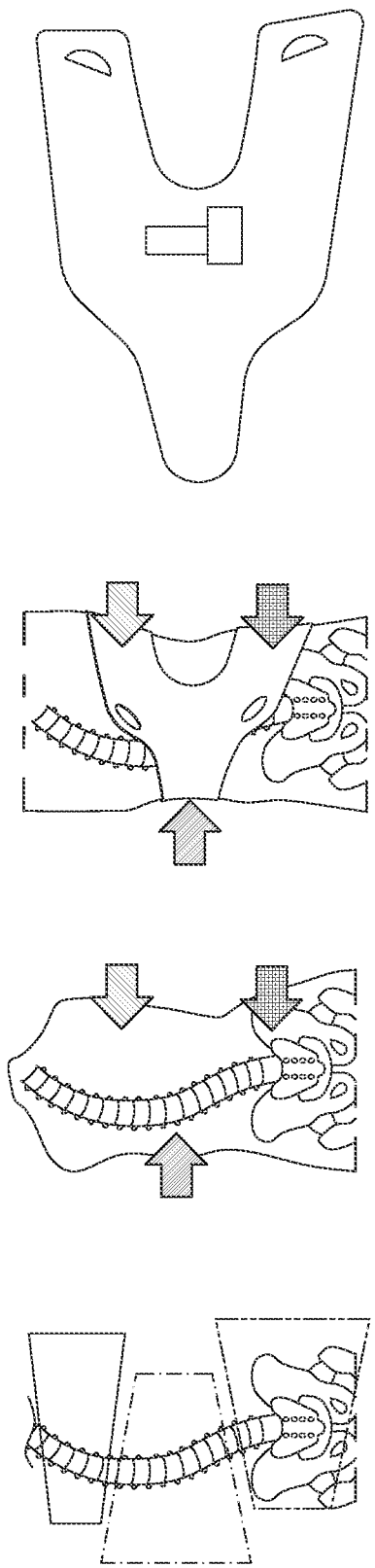
Figures 17A-17D - depict the Setup of the tension-based scoliosis system for a person with a Left Thoracic scoliosis curve.

Figures 18A-18B - show images having an adjustment of the lumbar belt in the back panel for a person with a Lumbar/Thoracolumar scoliosis curve.

Figures 19A-19B - show images of the setup of the lumbar belt in the back panel for a person with a Long Thoracic scoliosis curve.

SCOLIOSIS BRACE

CROSS REFERENCE TO RELATED APPLICATION

Application Ser. Nos. 62/873,845 ("the '845 application") and 62/873,846 ("the '846 application"), each of which is titled "Scoliosis Brace," and each of which is incorporated by reference herein in its entirety for all purposes.

BACKGROUND OF THE INVENTION

Field of the Invention

The invention relates to methods and apparatus of orthopedic correction, stabilization and support, and in a particular embodiment, to a Tension-based Scoliosis Orthosis, commonly known as a Scoliosis Brace, such as might be used to stabilize and correct a patient's spinal deformation. A preferred embodiment is directed to a tension-based scoliosis orthosis having a Y-shaped rigid back panel that generates continuous de-rotational forces in the transverse anatomical plane and translation forces in the coronal and sagittal planes. Proposed uses include orthopedic correction and stabilization of spinal deformations through a patient's daily, near-continuous, long-term wearing of the scoliosis brace.

Description of Related Art

Scoliosis is among the most common disorders of the spine, affecting approximately 3 in every 100 people worldwide [1]. Scoliosis presents itself as a misalignment of the spinal column, which is generally defined as a curve that deviates from the central spinal axis by greater than 10 degrees. While often simply characterized as a lateral curvature in the frontal plane, a rotational deformation about the transverse plane is common. For this reason, the various forms of scoliosis are more accurately described as complex three-dimensional deformities with misalignment occurring in the frontal and sagittal planes, as well as rotation in the transverse plane.

Scoliosis is a complex three-dimensional deformity of the spine, and there are two main types of adult scoliosis, the idiopathic and degenerative. According with Scoliosis Research Society (SRS) the adult idiopathic scoliosis is a prolongation of the adolescent idiopathic scoliosis (AIS), and the adult "De novo" degenerative scoliosis is a type of scoliosis that begins during the adult life due to arthritis and degeneration of the musculoskeletal system [2].

Adults with scoliosis can have more and a greater variety of symptoms compared with adolescents and younger patients. The adults have more symptoms because of the degeneration of the soft and hard tissues of the musculoskeletal system. The most common symptoms of adult scoliosis patients are back pain, stiffness, numbness, cramping and shooting pain in the legs, that can lead to gradual loss of function.

Aebi et al. classified adult scoliosis into three major types [3], all leading to an asymmetric breakdown of spinal discs and facet joints. Adults scoliosis can stem from one or more pathologies. The Type 1-3 classification scheme provided by Aebi, et al. [3] categorizes each based on the pathology that is thought to have led to the scoliosis. The Type 1 and Type 3 are the most clinically relevant groups. The Type 1 adult scoliosis is the degenerative scoliosis and is first seen late in life ("de novo") often after age 65 due to normal wear and tear on an aging spine. It is usually located in the thoracolumbar or lumbar spine and is often thought to express the mildest symptoms of the three cases [2] [3].

The treatment options for adult scoliosis patients are the conservative (non-operative) treatment for patients that don't have disabling symptoms, and the operative treatment for patients that failed the non-operative therapies and for patients that have restricted functional activities and substantially have reduced overall quality of life [2].

Bracing is an important modality of the non-operative treatment of scoliosis, principally in treatment of Adolescent Idiopathic Scoliosis (AIS). The main goal of bracing therapy for AIS patients is to prevent the progression and/or correct the scoliosis curves during the bone growth period. A rigid thoraco-lumbo-sacral orthosis (TLSO) is a brace worn to minimize progression of AIS. There are various TLSO designs (e.g., Boston, Milwaukee, Wilmington) [4]. The Boston brace is one kind of the traditional rigid braces and is the most frequently prescribed scoliosis braces for adolescents with idiopathic scoliosis. One limitation about the Boston brace is that it weakens the muscles and stiffens the spine. There are studies that found the traditional TLSO does not correct the three-dimensional deformity even though it reduces the cobb angle [6].

One another brace that is used for the conservative treatment of AIS is the Rigo-Cheneau type brace. Historically, the Cheneau-type brace was designed to oppose the spinal torsion and correct scoliosis in three dimensions [7]. The Cheneau type brace was developed approximately twenty-five years ago, with the main goal to combine biomechanical forces in three different anatomical planes [5], including de-rotations of the scoliosis curve in the transverse plane. Typically, the Rigo-Cheneau type brace has an open pelvis design with anterior opening [5]. Lebel et al found that in-brace Apical Vertebral Rotation (AVR) of scoliosis curve was significantly reduced by the Cheneau brace when compared to the TLSO brace" [8].

The Rigo-Cheneau Brace has proven more effective in three-dimensional correction of spinal curvature in cases of idiopathic scoliosis when compared to other contemporary methods (and its technical principles will therefore be taken as a standard in our analysis). Each case of scoliosis has its own unique curvature profile and the brace design is different for each case. There are three biomechanical principles that are implemented in order to move the trunk into the best-balanced position. These principles are three-point system in the frontal plane, de-rotation in the transverse plane, and physiological alignment in the sagittal plane. The general technique is to achieve morphological 3D correction by using a combination of forces applied to the trunk surface through specifically designed pads, facilitated by expansion spaces. There is a corrective reaction of the body in response to these forces, resulting in more improved posture and spinal alignment [7].

Research shows that braces that provide three-dimensional corrective forces produce better outcomes to prevent the progression or correct scoliosis [5][7] [8].

For adult patients, the main objectives of the bracing therapy are to provide relief of the symptoms and to promote a more balanced posture to improve the quality of life during daily living activities [2]. The existing scoliosis braces for adult patients available in the market don't provide an effective three-dimensional treatment of the scoliosis. This invention relates a three-dimensional tension-based scoliosis orthosis capable providing short term pain relief when in use and improvement of the spinal balance in scoliosis patients with different curve types. The disclosed bracing system is adjustable and personalized to provide the efficient three-dimensional correction to the specific curvature pattern of the patient.

SUMMARY OF THE INVENTION

The invention is directed to systems, methods, and apparatus involving scoliosis bracing using a three-dimensional support system capable of providing pain relief and improvement of the spinal balance in scoliosis patients with different curve types. The disclosed bracing system is a tension-based scoliosis orthosis that contains a rigid back panel. The rigid back panel generates continuous de-rotational forces in the transverse anatomical plane and translation forces in the coronal and sagittal planes. The de-rotational thoracic, lumbar and pelvic de-rotational supports/pads of the disclosed bracing system, provide facilitation or restriction of certain movements of human spine in the coronal, sagittal and transverse planes. The scoliosis bracing system may be used in cases of, for instance, idiopathic scoliosis and degenerative scoliosis. Moreover, the invention is also effective in treating postural abnormalities and unbalances of the spine wherein the ability to maintain more balanced and improved posture of the trunk, pelvis and shoulder girdle.

This tension-based scoliosis system is adjustable and personalized to provide an efficient three-dimensional support to the specific curvature pattern of the patient. The adjustability of supportive/compression/pressure and tension forces are achieved by incorporating the design of the rigid back panel, attaching pads and strapping system. This bracing system generates a three point of pressure that is able to apply appropriate forces in the transversal plane, coronal plane and sagittal plane wherever it is needed for a given case as determined by the physician. With the appropriate determination of the direction and magnitude of the pressure from the bracing system, the rotational aspect of the scoliosis can also be corrected. The hole system performs the sufficient pressure to support and stabilize an imbalanced trunk, and also restrict or facilitate the ability of patients to move. The mechanical properties of the back panel and strap system have a high strength to provide the appropriate support/compression and sufficient tension.

This tension-based scoliosis system provides also proprioceptive feedback of the trunk muscles, which helps to develop muscular memory so that the body can actively correct posture when the system is not in use.

The disclosed tension-based scoliosis system is lightweight and portable for frequent or daily use, while easily custom fitted. The design this bracing system is simple, allowing the patients to easily wear and take off the brace every day without assistance.

The materials of this support system are biocompatible and hypoallergenic due to the possibility of direct contact with user's skin. To ensure proper hygiene the brace can be washable. The long-time wearing of the brace should not stiffen the muscle and cause inflammation of the skin. The brace design has also a function to reduce the side effects of insufficient blood supply and limited breath, which exist in current products. In order to mitigate pressure points the brace design doesn't have any sharp edges or corners.

Further aspects of the invention are set forth herein. The details of exemplary embodiment of the invention are set forth in the accompanying drawings and description below.

Other features, objects, and advantages of the invention will be apparent from the description and drawings, and from the claims.

BRIEF DESCRIPTION OF THE DRAWINGS

By reference to the appended drawings, which illustrate an exemplary of the embodiment of this invention, the detailed description provided below explains in details various features, advantages and aspects of this invention. As such, features of this invention can be more clearly understood from the following detailed description considered in conjunction with the following drawings, in which the same reference numerals denote the same elements throughout. The exemplary embodiment illustrated in the drawings is not necessary to scale and is not to be considered limiting of its scope, for the invention may admit to other equally effective embodiments.

FIG. 1 shows a plan view image of a front side of an exemplary embodiment of the invention.

FIG. 2 shows a plan view image of a back side the exemplary embodiment of FIG. 1.

FIG. 3A shows a plan view image of a rigid back panel of the exemplary embodiment of FIG. 1, and FIGS. 3B and 3C show perspective view images of adjustable Velcro hook and loop system/fasteners on an inner face of a back piece that will attach with a lumbar belt of FIG. 1.

FIG. 5A depicts an illustration of a typical posterior view of an x-ray of a person with a left lumbar/thoracolumbar scoliosis and the relationship of scoliosis concavity and convexity with different structural blocks of the spine. FIG. 5B depicts an illustration of directions of the rotation of the thoracic block, lumbar block and pelvis block of a person with a left lumbar/thoracolumbar scoliosis curve. FIG. 5C depicts a typical posterior view of a body of a person with a left lumbar/thoracolumbar scoliosis.

FIG. 6A depicts a typical posterior view of a body of a person with a left lumbar/thoracolumbar scoliosis and its relationship with the convexity and concavity of the scoliosis curve. FIG. 6B depicts a slice of the transverse anatomical plane of patient body at the apex of a left lumbar/thoracolumbar scoliosis. FIG. 6C depicts an illustration of appropriate application of the de-rotational forces of the scoliosis bracing system to a person with a left lumbar/thoracolumbar scoliosis.

FIGS. 7A-7B depicts de-rotation forces applied in a wearer body with left lumbar/thoracolumbar scoliosis. Each de-rotational force has two components, the component of the coronal plane and the component of the sagittal plane.

FIGS. 9A-9B depicts illustrations of components of the de-rotational forces that are to be applied in the sagittal plane.

FIG. 11A depicts a typical posterior view of a body of a person with a left lumbar/thoracolumbar scoliosis and its relationship with the three-point pressure in the coronal plane. FIGS. 11B-11C show images of a setup of the disclosed tension-based scoliosis system for a person with a left lumbar/thoracolumbar scoliosis curve.

FIG. 12 shows images of a preferred sequence of a wearer donning the brace, in which the bracing system was adapted for a left lumbar/thoracolumbar scoliosis curve.

FIG. 13 shows images of an adjustment of strap tension of the de-rotational forces of a thoracic pad.

FIG. 14 shows images of an adjustment of strap tension of the de-rotational forces of a pelvis pad.

FIGS. 17A-17D show a setup of the tension-based scoliosis system for a person with a left thoracic scoliosis curve.

FIGS. 18A-18D show images of an adjustment of a lumbar belt in the back panel for a person with a lumbar/thoracolumbar scoliosis curve.

LISTING OF DRAWING REFERENCES AND NUMERALS

Figure 4B:
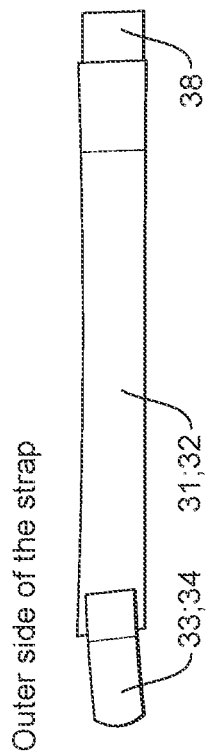
FIGS. 4A-4D show images of adjustment straps adapted to be connected to de-rotational pads of the tension-based scoliosis orthosis embodiment of FIG. 2.

Group 1—Back Panel
10—Y-shaped rigid/semi-rigid back panel
11—V1 De-rotational pad of the back panel
12—Y De-rotational pad of the back panel
13—V2 De-rotational pad of the back panel
14—"D" hole of the V1 De-rotational pad
15—"D" hole of the V1 De-rotational pad
16—Hole for the attachment of the lumbar belt—The lumbar belt will attach to the back panel through this hole.
17—The adjustable Velcro hook and loop system/fastener on the inner face of the back piece that will attach with the lumbar belt.
Group 2—Lumbar Belt
20—Semi-rigid lumbar belt
21—V arm of the lumbar belt
22—Y arm of the lumbar belt
23—Velcro Hook of the V arm of the lumbar belt
24—Cord system Y side of the lumbar belt
25—Cord system of the V side of the lumbar belt
26—Pull tab cord system of the V side of the lumbar belt that contains a Velcro hook that will attach to the Velcro loop fabric of the outer side of the belt.
27—Pull tab cord system of the Y side of the lumbar belt that contains a Velcro hook that will attach to the Velcro loop fabric of the outer side of the belt.
28—Cover of the cord system of the lumbar belt.
29—The outer side of the arms of the lumbar belt are made with a Velcro hook fabric.
210—The fabric permanently sewn in the lumbar belt that is going to attach to the back panel and attach to the cover of the back panel through
Group 3—Straps of De-Rotational Pads
31—V1 Strap of the de-rotation pad
32—V2 Strap of the de-rotational pad
33—Removable Velcro hook V1 strap
34—Removable Velcro hook V2 strap
35—Velcro hook permanently sewn on the distal end of V1 strap
36—Velcro hook permanently sewn on the distal end of V2 strap
37—Proximal end of the strap without the removable hook
38—Nylon fabric sewn in the distal edge of the strap
Group 4—Cover of back panel
40—Cover of the rigid/semi rigid back panel made of foam and polyester mesh
41—Elastic fabric to attach the cover made of foam and polyester mesh to the V1 de-rotational pad of the back panel.
42—Elastic fabric to attach the cover made of foam and polyester mesh to the V2 de-rotational pad of the back panel.
43—Elastic fabric to attach the cover made of foam and polyester mesh to the Y de-rotational pad of the back panel.
44—The posterior section of the back-panel cover is made from polyester fabric with Velcro loop and is in contact with inner face of the back panel.

DETAILED DESCRIPTION

As shown in FIG. 1 and FIG. 2, an exemplary of the tension-based scoliosis orthosis according to the invention may include, for example: a rigid/semi-rigid back panel 10; a lumbar belt 20 connected to the rigid back panel; a cover 40 of the rigid/semi-rigid back panel; and the V1 strap 31 and V2 strap 32 connected to the rigid/semi-rigid back panel. The V1 strap 31 and the V2 strap 32 and any other disclosed strap may be made, for instance, of durable nylon, polyester, rayon, cotton, leather, pliable resin, pliable rubber, woven fabric, etc.

FIGS. 1 and 2 show the V arm 21 and the Y arm 22 of the lumbar belt 20. FIG. 1 shows the sewn Velcro hook 23 in the V arm 21 of the lumbar belt. The fabric on the outer side of the lumbar belt is made from a fabric with Velcro loop, shown in FIG. 2.

FIG. 3A shows the rigid/semi-rigid back panel 10. The back panel in one side has two de-rotational pads, the V1 de-rotational pad 11 and the V2 de-rotational pad 13 and in the other side has one de-rotational pad, the Y de-rotational pad 12. The back panel has a "D" hole 14 in the V1 de-rotational pad 11 and a "D" hole 15 in the V2 de-rotational pad. The V1 strap 31 and V2 strap 32 are going to attach to the de-rotational pads of the back panel through the "D" holes 14 and 15 respectively. FIG. 3A is shown the hole 16 that was developed to create the adjustable Velcro hook and loop system/fastener.

FIGS. 3B and 3C show the adjustable Velcro hook and loop system/fastener 17 on the inner face of the rigid/semi-rigid back panel that will attach to the small durable nylon/polyester strap 210 permanently sewn in the lumbar belt 20. The rigid/semi-rigid back panel 10 and de-rotational straps 31 and 32 of this invention are the cores of the improved tension-based scoliosis orthosis and these components 10, 31 and 32 can be attached and adapted to other types of lumbar belts through the adjustable Velcro hook and loop system/fastener. FIGS. 3B and 3C show the side 211 of the strap 210 that is going to attach to the Velcro hook that is in the inner face of the back panel 17. FIG. 2 shows posterior section 44 of the cover 40 of the back panel. The posterior section 44 of the back-panel cover made from polyester fabric with Velcro loop and is in contact with inner face of the back panel. FIGS. 3B and 3C shows the Velcro hook 212 of the strap 210 of the lumbar belt 20 that is going to attach to the Velcro loop 44 of the cover of the back panel.

Figure 4D:
Figure 4A:
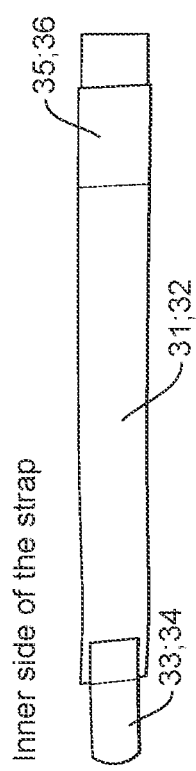
Figure 4C:
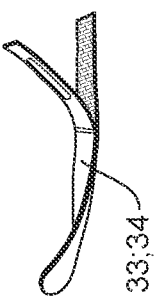

FIGS. 4A and 4B shows the detailed view of V1 strap 31 and V2 strap 32 that are going to attach to the de-rotational pads of the back panel, 11 and 13 respectively and to the outer section of the V arm 21 of the lumbar belt 20. For custom fit and for an optimal adjustment of the tension of the straps V1 31 and V2 32, a health care professional can remove the Velcro hook piece 33 and/or 34 that is in the proximal end 37 of the strap shown in FIGS. 4C and 4D. The professional health care can customize/trim the size of the strap accordingly with the patient size, patient characteristics, scoliosis curve pattern and degree of deformity. After customization of the straps, the professional health care can setup, attach and adjust the straps in the de-rotational pads of the rigid/semi-rigid back panel 10 and lumbar belt 20. FIGS. 1 and 2 show the V1 strap 31 and V2 strap 32 attached to the rigid/semi-rigid back panel through the "D" holes 14 and 15. The removable Velcro hook 33 and 34 along the proximal end of the straps allows easy adjustment about the length. The Velcro hook pieces 35 and 36 permanently sewn on the distal end of V1 strap 31 and on the distal end of V2 strap 32 are going to be fixed in the Velcro loop of the outer side of V arm 21 of the lumbar belt 20, shown in FIG. 2.

To understand better the application of the disclosed invention is described an application of this improved tension-based scoliosis system to a body of a wearer with a left lumbar/thoracolumbar scoliosis. FIG. 5A shows a typical posterior view of an x-ray of a person with a left lumbar/thoracolumbar scoliosis and its relationship with the different structural blocks of the spine, pelvis, lumbar/thoracolumbar and thoracic. FIG. 5B illustrates de direction of the rotation of the structural blocks of the spine of a person with a left lumbar/thoracolumbar scoliosis. For this specific scoliosis curve pattern of a left lumbar/thoracolumbar curve, when viewing the transverse plane from the top the lumbar/thoracolumbar block is rotated in the anti-clockwise direction and the thoracic and pelvis blocks are rotated in the clockwise direction. FIG. 6A shows typical posterior view of a deformed body of a person with a left lumbar/thoracolumbar scoliosis and its relationship with the convexity and concavity of the scoliosis curve. FIG. 6B shows an illustration of a slice of the transverse plane of the body of the patient at the apex of a left lumbar/thoracolumbar curve. FIG. 6C illustrates the appropriate application of the supportive forces of the bracing system in a body of a person with a left lumbar/thoracolumbar scoliosis. The thoracic, lumbar and pelvis pads are going to de-rotate the structural blocks of the spine in the opposite direction of the scoliosis deformity.

FIGS. 7A-7B illustrates the de-rotational forces that the disclosed tension-based scoliosis tension system is going to apply in a body of a wearer with a left lumbar/thoracolumbar scoliosis. The de-rotational forces are going to de-rotate the spine in the transverse plane and subsequent align the spinal segments in the frontal, transverse and sagittal planes.

Each de-rotational force has two components, the component of the coronal plane and the component of the sagittal plane. The V1 de-rotational pad 11 is going to apply the force Fv1 in the thoracic block, the Y de-rotational pad 12 is going to apply the force FY in the lumbar/thoracolumbar block and the V2 de-rotational pad 13 is going to apply the force FV2 in the Pelvis block.

Figure 8A:
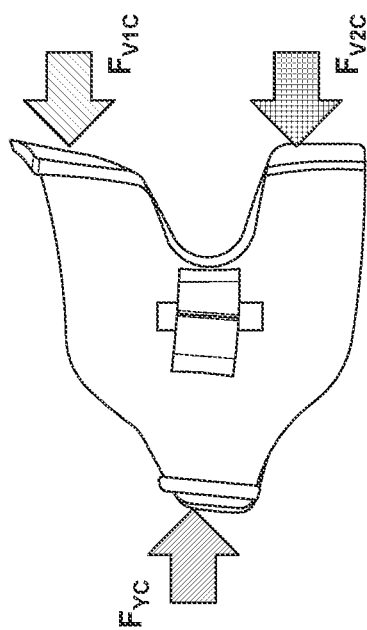
FIGS. 8A-8B show components of the de-rotational forces that the back panel of FIG. 3A is adapted to form in the coronal plane using a three-point pressure/force system.
Figure 8B:
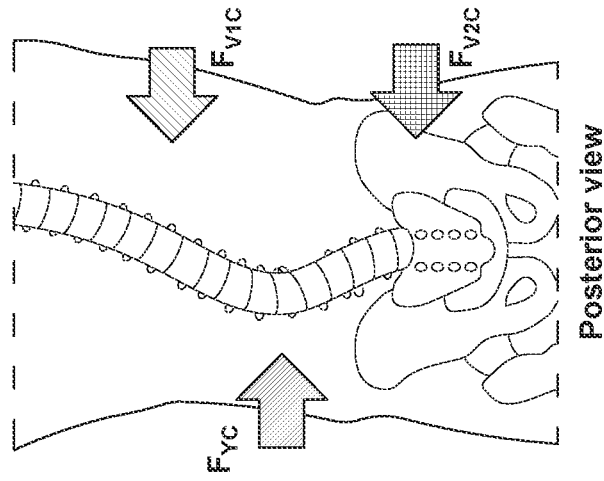

FIGS. 8A-8B shows the components of the de-rotational forces that are going to form the three-point pressure system in the coronal plane. In traditional scoliosis bracing a three-point force system is formed by a corrective force and two counterforces applied proximally and distally as shown in FIG. 8B. The Y de-rotational pad 12 is going to apply a corrective/supportive force FYC at the apex of the convexity of the scoliosis curve. The V1 de-rotational pad 11 going to apply a counterforce Fv1C in the proximal end of the concave side of the of the scoliosis curve. The V2 de-rotational pad 13 is going to apply a counterforce Fv2C in the distal end of the concave side of the of the scoliosis curve.

FIGS. 9A-9B shows the components of the de-rotational forces in the sagittal plane. The force FV1S of the V1 de-rotation pad 11 is going to de-rotate the thoracic block in the anti-clockwise direction. The force FYS of the Y de-rotation pad 12 is going to de-rotate the lumbar block in the clockwise direction. The force FV2S of the V2 de-rotation pad 13 is going to de-rotate the pelvis block in the anti-clockwise direction.

Figure 10A:
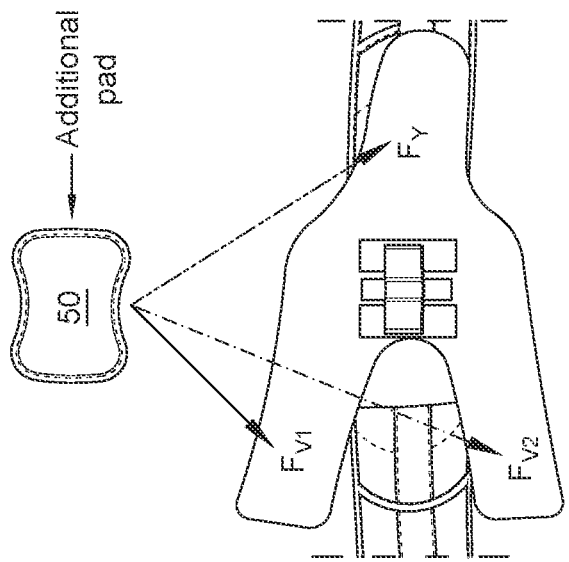
FIGS. 10A-10C depict illustrations and an image of preferred adjustment of the direction and magnitude of the de-rotational forces by using additional pads.
Figure 10B:
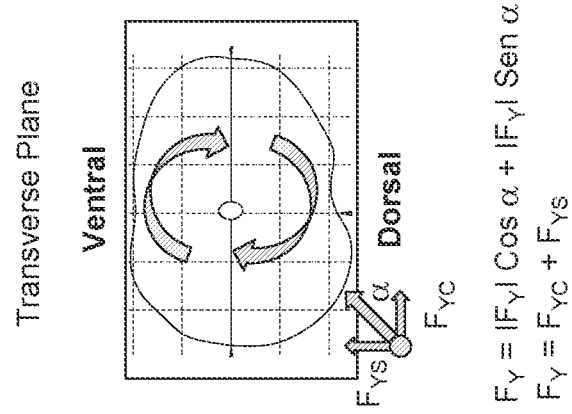
Figure 10C:
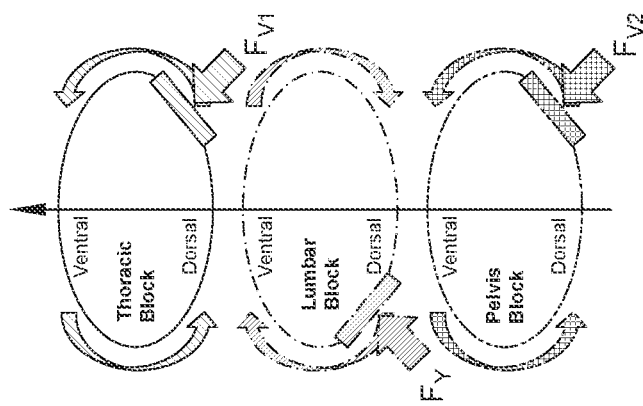
Figure 15D:
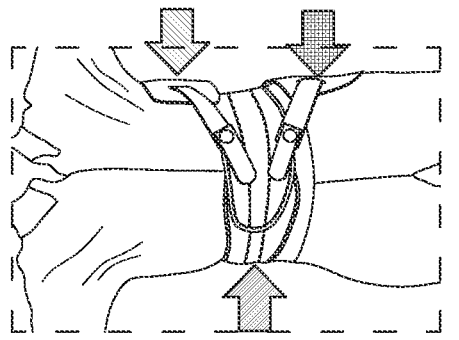
FIGS. 15A-15D show a setup of the tension-based scoliosis system for a person with right lumbar/thoracolumbar scoliosis.
Figure 15C:
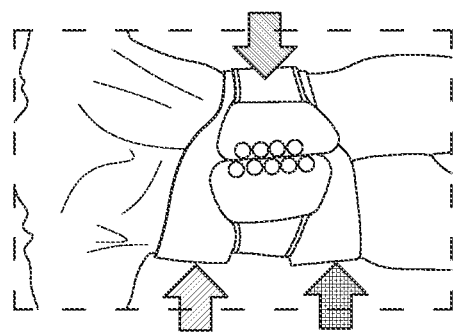
Figure 15B:
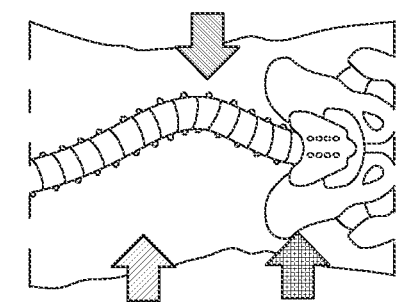
Figure 15A:
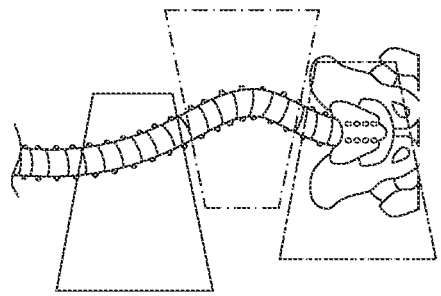
Figure 16A:
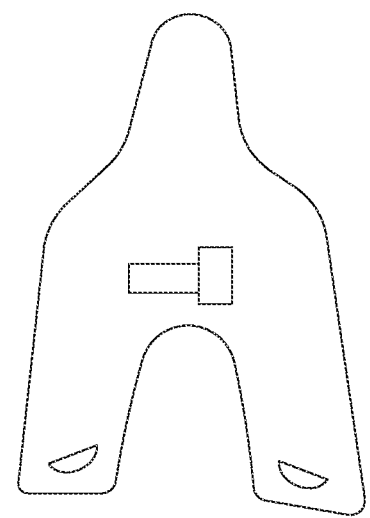
FIGS. 16A-16B show a setup of the tension-based scoliosis system for a person with a right thoracic scoliosis curve.
Figure 16B:
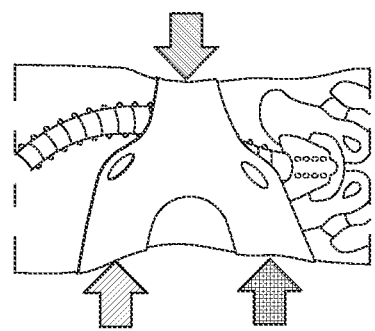
Figure 16C:
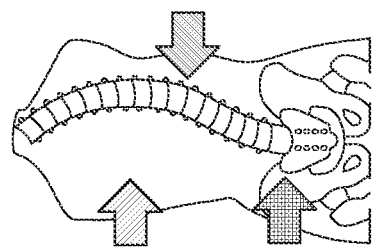
Figure 16D:
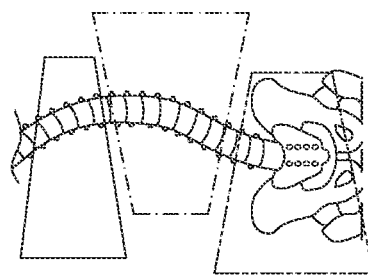

FIGS. 10A-10C show illustrations how to adjust the direction and magnitude of the de-rotational forces by using additional pads. FIG. 10C shows the additional pad 50 that can be added and placed in the inner face of the rigid/semi-rigid back panel 10 and under the cover 40. The pad 50 may be placed more laterally or more posteriorly depending of the magnitude of the rotation or translation that the patient needs to achieve a more balanced position of the spine and improved posture.

FIGS. 11A-11C shows posterior and anterior view of the setup of the disclosed tension-based scoliosis system for a person with a left lumbar/thoracolumbar scoliosis. The geometric configuration and orientation of both straps 31 and 32 is highly adjustable. The bracing system is restricting the movement of side bending of the spine to the right side and facilitating the movement of side bending to the left. The tension-based scoliosis system is restricting the rotation of the thoracic block and pelvic block in the clockwise direction and facilitating the movement of rotation in the anti-clockwise direction. The tension-based scoliosis system is restricting the rotation of the lumbar/thoracolumbar block in the anti-clockwise direction and facilitating the movement of rotation in the clockwise direction.

FIG. 12 shows the steps of a wearer putting the brace on. On step 1 the wearer holds the distal end of the V arm 21 and the distal end of the Y arm 22 of the lumbar belt 20 wrapping around the rigid/semi-rigid back panel 10 to provide consistent and strong support to the back, keeping the rigid/semi-rigid back panel 10 flush to the body of the wearer. There's a pulling system on the outer surface of the belt 20. The two pulling tabs 26 and 27 of are two major components of the pulling system, which are used to adjust the tightness of the belt. The belt 20 gets tighter as the tabs are being pulled. The pelvic belt 20 applies compression to torso at lumbar level to achieve lumbar alignment with the use of the sagittal profile of back panel 10. The compressive belt 20 transmits force to an Y de-rotational pad 13 of the rigid/semi-rigid back panel 10, de-rotating the lumbar block in the transverse plane in the clock-wise direction and creating a lateral force FYC in the coronal plane toward the medial axis, shown in FIGS. 8A-8B.

FIG. 13 shows the adjustment of the tension of the V1 strap 31 of the V1 de-rotational pad 11. Tightness of the V1 strap 31 can be adjusted by attaching the Velcro hook 35 on the different Velcro loop sections of the V arm 21 of the pelvic belt that are on the same level but different distance relative to the front center line. The V1 strap 31 that is attached to the V1 de-rotational pad 11 of the rigid/semi-rigid back panel 10, which impart force onto the right thoracic section of the body is de-rotating the thoracic block in the transverse plane in the anti-clockwise direction and creating a lateral force FV1C in the coronal plane toward the medial axis, as shown in FIGS. 8A-8B. As shown in FIGS. 10A-10C a pad may be placed in the inner face of the V1 de-rotational pad 11 to adjust the direction and/or increase the magnitude of the de-rotational force FV1.

FIG. 14 shows the adjustment of the tension of the V2 strap 32 of the V2 de-rotational pad 13. Tightness of the V2 strap 32 can be adjusted by attaching the Velcro hook 36 on the different Velcro loop sections of the V arm 21 of the pelvic belt that are on the same level but different distance relative to the front center line. The V2 strap 32 that is attached to the V2 de-rotational pad 13 of the rigid/semi-rigid back panel 10, which impart force onto the right pelvis section of the body is de-rotating the pelvis block in the transverse plane in the anti-clockwise direction and creating a lateral force FV2C in the coronal plane toward the medial axis, as shown in FIGS. 8A-8B. As shown in FIGS. 10A-10C a pad may be placed in the inner face of the V2 de-rotational pad 13 to adjust the direction and/or increase the magnitude of the de-rotational force FV2.

FIGS. 15A-15D show the setup of the disclosed tension-based scoliosis system for a person with a right lumbar/thoracolumbar scoliosis. FIGS. 16A-16D show the Setup of the tension-based scoliosis system for a person with a Right Thoracic scoliosis curve. FIGS. 17A-17D show the Setup of the tension-based scoliosis system for a person with a Left Thoracic scoliosis curve.

Figures 18A, 18B:
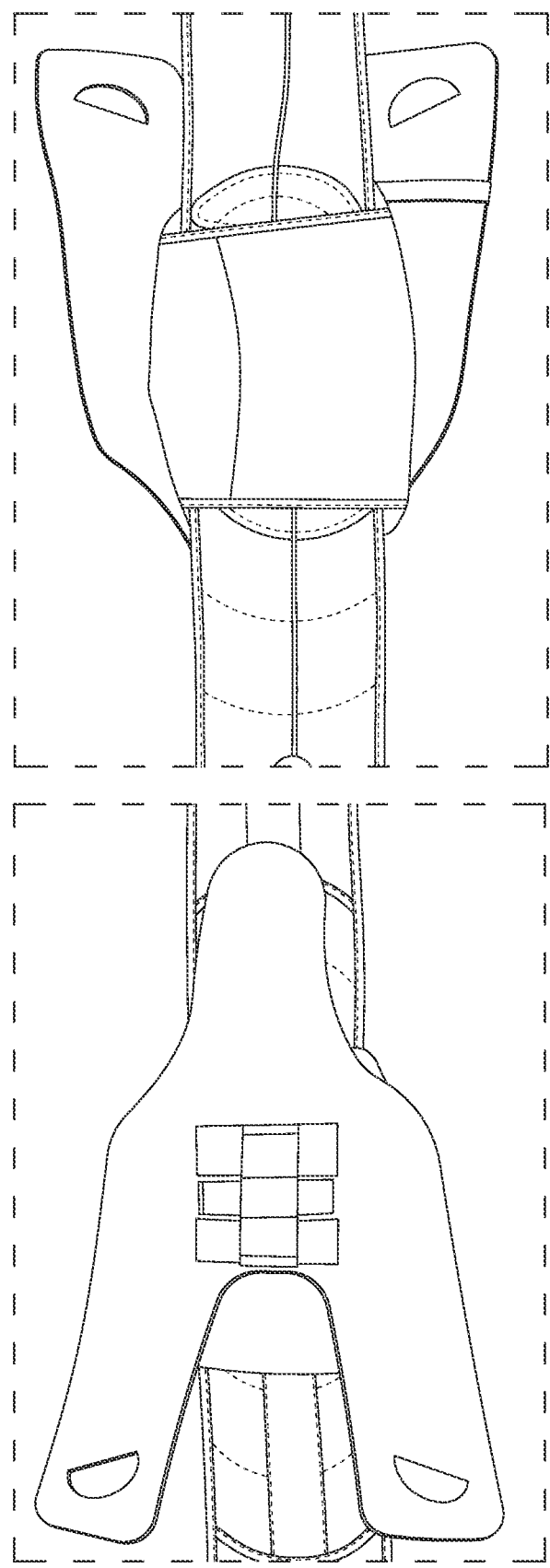

FIGS. 18A-18B show the adjustment of the lumbar belt 20 on the back panel 10 for a person with a Lumbar/Thoracolumbar scoliosis curve. The adjustment of the lumbar belt on the panel is made through the adjustable Velcro hook and loop system/fastener of the inner face of the back panel, as shown in FIGS. 3B and 3C. Typically for these curve types the apex of the convexity of the scoliosis curve is located at the level of the lumbar/thoracolumbar block. The belt has to fixed in the center of the hole 16 of the back panel, so the Y de-rotational pad 12 will match with the apex of the scoliosis curve.

Figure 19A:
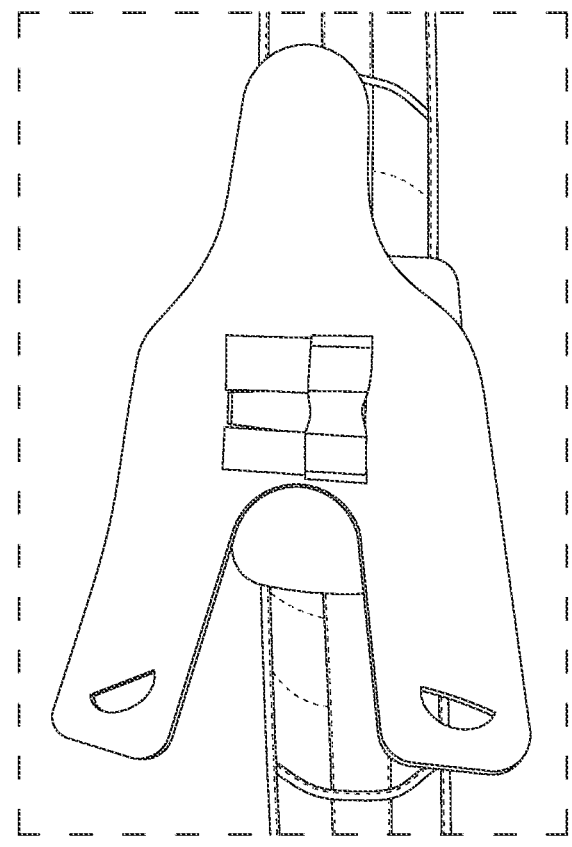
FIGS. 19A-19B show images of an adjustment of a lumbar belt in the back panel for a person with a long thoracic scoliosis curve.
Figure 19B:
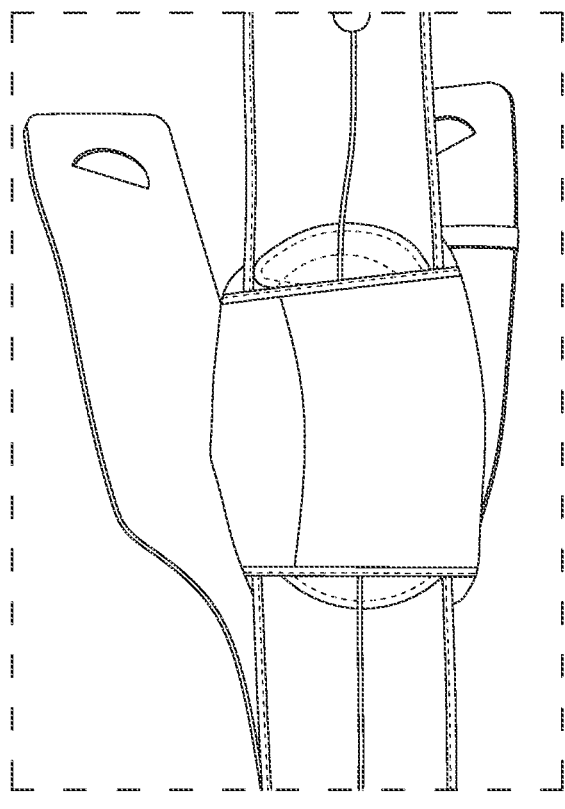

FIGS. 19A-19B show the adjustment of the lumbar belt 20 on of back panel 10 for a person with a long thoracic scoliosis curve. The adjustment of the lumbar belt on the panel is made through the adjustable Velcro hook and loop system/fastener of the inner face of the back panel, as shown in FIGS. 3B and 3C. Typically for these curve types the apex of the convexity of the scoliosis curve is located at the level of the thoracic block and we have to adjust the three-point pressure of the bracing system in higher level of the spine. The belt has to fixed in the lower section of the hole 16 of the back panel, so the Y de-rotational pad 12 will match with the apex of the scoliosis curve.

The foregoing description discloses exemplary embodiments of the invention. While the invention herein disclosed has been described by means of specific embodiments and applications thereof, numerous modifications and variations could be made thereto by those skilled in the art without departing from the scope of the invention set forth in the claims. Modifications of the above disclosed apparatus and methods that fall within the scope of the claimed invention will be readily apparent to those of ordinary skill in the art. Accordingly, other embodiments may fall within the spirit and scope of the claimed invention, as defined by the claims that follow hereafter.

In the description above, numerous specific details are set forth in order to provide a more thorough understanding of embodiments of the invention. It will be apparent, however, to an artisan of ordinary skill that the invention may be practiced without incorporating all aspects of the specific details described herein. Not all possible embodiments of the invention are set forth verbatim herein. A multitude of combinations of aspects of the invention may be formed to create varying embodiments that fall within the scope of the claims hereafter. In addition, specific details well known to those of ordinary skill in the art have not been described in detail so as not to obscure the invention. Readers should note that although examples of the invention are set forth herein, the claims, and the full scope of any equivalents, are what define the metes and bounds of the invention protection.

REFERENCES

[1]: Scoliosis. (n.d.). Retrieved Dec. 10, 2017, from http://www.aans.org/Patients/Neurosurgical-Conditions-and-Treatments/Scoliosis

[2]: Conditions and Treatments for Adult Scoliosis. (n.d.). Retrieved Jul. 5, 2019, from https://www.srs.org/patients-and-families/conditions-and-treatments/adults/scoliosis

[3]: Aebi M. The adult scoliosis. Eur Spine J. 2005; 14(10): 925-948. doi: 10.1007/s00586-005-1053-9.

[4]: Zaina F, De Mauroy J C, Grivas T, Hresko M T, Kotwizki T, Maruyama T, Price N, Rigo M, Stikeleather L, Wynne J, Negrini S. Bracing for scoliosis in 2014: state of the art. Eur J Phys Rehabil Med. 2014; 50(1):93-110.

[5]: Minsk et al. Scoliosis and Spinal Disorders. 2017; 12:7D01 10.1186/s13013-017-0117-z

[6]: Labelle H(1), Dansereau J, Bellefleur C, Poitras B. Three-dimensional effect of the Boston brace on the thoracic spine and rib cage. Spine (Phila Pa. 1976). 1996 Jan. 1; 21(1):59-64.

[7]: Rigo and Jelačié Scoliosis and Spinal Disorders. (2017) 12:10. DOI 10.1186/s13013-017-0114-2

[8]: Lebel D E(1), Al-Aubaidi Z, Shin E J, Howard A, Zeller R. Three-dimensional analysis of brace biomechanical efficacy for patients with AIS Eur Spine J. 2013 November; 22(11):2445-8. doi: 10.1007/s00586-013-2921-3. Epub 2013 Jul. 20.

We claim:

1. A scoliosis brace comprising a lumbar belt and a back panel attached to the lumbar belt, wherein the back panel has a Y shape, the Y shape having a trunk section and two branch sections, and includes three de-rotational pads, with one de-rotational pad at each section of the Y shape, wherein the Y shape is adapted to horizontally span a wearer's back from a first side of the wearer to a second side of the wearer when the wearer wears the brace, with the trunk section adapted to support the first side and the two branch sections adapted to support the second side, wherein each de-rotational pad of the two branch sections includes an adjustable adjustment strap that is adapted to connect to the lumbar belt, and wherein the lumbar belt includes a pull-tab cord system adapted to adjust and tighten the lumbar belt according to the wearer's physique.

2. A method of providing a scoliosis brace, the method comprising:
   providing a lumbar belt, and;
   providing a back panel attached to the lumbar belt,
   wherein the back panel has a Y shape, the Y shape having a trunk section and two branch sections, and includes three de-rotational pads, with one de-rotational pad at each section of the Y shape;
   wherein the Y shape is adapted to horizontality span a wearer's back from a first side of the wearer to a second side of the wearer when the wearer wears the brace, with the trunk section adapted to support the first side and the two branch sections adapted to support the second side;

wherein each de-rotational pad of the two branch sections includes an adjustable adjustment strap that is adapted to connect to the lumbar belt, and wherein the lumbar belt includes a pull-tab cord system adapted to adjust and tighten the lumbar belt according to the wearer's physique.

3. The scoliosis brace of claim 1, wherein the back panel includes an intersection of the trunk section and the two branch sections, and the intersection is adapted to be positioned proximate a center of the wearer's back when the wearer wears the brace.

4. The scoliosis brace of claim 1, wherein the back panel includes a space located vertically between the two branch sections and formed by the two branch sections separating and extending from an intersection with the trunk section, and the space is adapted to be positioned proximate the first side of the wearer or the second side of the wearer when the wearer wears the brace.

5. The scoliosis brace of claim 1, wherein the back panel is curved, is semi-rigid or rigid, and includes a cover that covers an inner face of the back panel that faces the wearer.

6. The scoliosis brace of claim 1, wherein the back panel includes a D-shaped hole at each de-rotational pad of each branch section, and the adjustable strap of each de-rotational pad is attachable to the de-rotational pad through the D-shaped hole.

7. The scoliosis brace of claim 1, wherein the back panel includes an attachment hole proximate an intersection of the trunk section and the two branch sections, and the attachment hole is adapted for use in attaching the back panel to the lumbar belt.

8. The scoliosis brace of claim 7, wherein the back panel includes a fastener on an inner face of the back panel, the fastener is affixed laterally to the attachment hole, and the fastener is adapted to receive a corresponding fastener from the lumbar belt tor use in attaching the back panel to the lumbar belt.

9. The scoliosis brace of claim 8, wherein the fastener of the back panel and the corresponding fastener from the lumbar belt are adapted to be aligned and adjusted in more than one orientation when attaching the back panel to the lumbar belt, and each orientation is adapted to create a specific geometric configuration or de-rotational pads to apply specific corrective or supportive forces for a specific scoliosis curve of the wearer.

10. The scoliosis brace of claim 9, wherein the fastener of the back panel and the corresponding fastener from the lumbar belt are adapted to be aligned and adjusted to configure the de-rotational pads respectively as thoracic, lumbar, and pelvic pads that respectively are adapted to apply de-rotational forces at and to thoracic, lumbar, and pelvic regions of the wearer, in which said de-rotational forces are adjustable appropriately to the specific scoliosis curve of the wearer by adjusting the adjustable straps and the lumbar belt.

11. The method of claim 2, wherein the back panel includes an intersection of the trunk section and the two branch sections, and the intersection is adapted to be positioned proximate a center of the wearer's back when the wearer wears the brace.

12. The method of claim 2, wherein the back panel includes a space located vertically between the two branch sections and formed by the two branch sections separating and extending from an intersection with the trunk section, and the space is adapted to be positioned proximate the first side of the wearer or the second side of the wearer when the wearer wears the brace.

13. The method of claim 2, wherein the back panel is curved, is semi-rigid or rigid, and includes a cover that covers an inner face of the back panel that faces the wearer.

14. The method of claim 2, wherein the back panel includes a D-shaped hole at each de-rotational pad of each branch section, and the adjustable strap of each de-rotational pad is attachable to the de-rotational pad through the D-shaped hole.

15. The method of claim 2, wherein the back panel includes an attachment hole proximate an intersection of the trunk section and the two branch sections, and the attachment hole is adapted for use in attaching the back panel to the lumbar belt.

16. The method of claim 15, wherein the back panel includes a fastener on an inner face of the back panel, the fastener is affixed laterally to the attachment hole, and the fastener is adapted to receive a corresponding fastener from the lumbar belt for use in attaching the back panel to the lumbar belt.

17. The method of claim 16, wherein the fastener of the back panel and the corresponding fastener from the lumbar belt are adapted to be aligned and adjusted in more than one orientation when attaching the back panel to the lumbar belt, and each orientation is adapted to create a specific geometric configuration of de-rotational pads to apply specific corrective or supportive forces for a specific scoliosis curve of the wearer.

18. The method of claim 17, wherein the fastener of the back panel and the corresponding fastener from the lumbar belt are adapted to be aligned and adjusted to configure the de-rotational pads respectively as thoracic, lumbar, and pelvic pads that respectively are adapted to apply de-rotational forces at and to thoracic, lumbar, and pelvic regions of the wearer, in which said de-rotational forces are adjustable appropriately to the specific scoliosis curve of the wearer by adjusting the adjustable straps and the lumbar belt.

19. A scoliosis brace back panel for use with a scoliosis brace, the back panel comprising:

a single solid curved back piece that is semi-rigid or rigid and adapted to be adjustably attached to a lumbar belt;

wherein the back piece has a Y shape;

wherein the Y shape has a trunk section and two branch sections;

wherein the back piece includes three de-rotational pads, with one de-rotational pad at a distal portion of each section of the Y shape;

wherein the Y shape is adapted to horizontally span a wearer's back from a first side of the wearer to a second side of the wearer when the wearer wears the brace, with the trunk section adapted to support the first side and the two branch sections adapted to support the second side;

wherein each de-rotational pad of the two branch sections is adapted to receive and attach to an adjustable adjustment strap, in which the adjustable adjustment strap, once attached to the branch section, is adapted to connect to the lumbar belt, and adapted to be adjusted and tightened to the lumbar belt according to the wearer's physique, once the back panel is attached to the lumbar belt.

20. The scoliosis brace back panel of claim 19:

wherein the back piece includes an intersection of the trunk section and the two branch sections, and the intersection is adapted to be positioned proximate a center of the wearer's back when the wearer wears the brace;

wherein the back piece includes a space located vertically between the two branch sections and formed by the two branch sections separating and extending from the intersection with the trunk section, and the space is adapted to be positioned proximate the first side of the wearer or the second side of the wearer when the wearer wears the brace;

wherein the back piece includes a D-shaped hole at each de-rotational pad of each branch section, and the adjustable strap of each de-rotational pad is adapted to be attached to the de-rotational pad through the D-shaped hole;

wherein the back piece includes an attachment hole proximate the intersection of the trunk section and the two branch sections, and the attachment hole is adapted for use in attaching the back panel to the lumbar belt; and wherein the back piece includes a fastener on an inner face of the back piece, the fastener is affixed laterally to the attachment hole, and the fastener is adapted to receive a corresponding fastener from the lumbar belt for use in attaching the back panel to the lumbar belt.

\* \* \* \* \*